(12) United States Patent
Seo et al.

(10) Patent No.: US 8,617,857 B2
(45) Date of Patent: Dec. 31, 2013

(54) THRAUSTOCHYTRID-BASED MICROALGAE, AND METHOD FOR PREPARING BIO-OIL BY USING SAME

(75) Inventors: Jeong-Woo Seo, Daejeon (KR); Chul Ho Kim, Daejeon (KR); Dina Rairakhwada, Daejeon (KR); Won Kyung Hong, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 0 days.

(21) Appl. No.: 13/695,416

(22) PCT Filed: Apr. 25, 2011

(86) PCT No.: PCT/KR2011/002999
§ 371 (c)(1),
(2), (4) Date: Dec. 11, 2012

(87) PCT Pub. No.: WO2011/139040
PCT Pub. Date: Nov. 10, 2011

(65) Prior Publication Data
US 2013/0089901 A1    Apr. 11, 2013

(30) Foreign Application Priority Data

May 4, 2010   (KR) .................. 10-2010-0041942
May 4, 2010   (KR) .................. 10-2010-0041944
Nov. 24, 2010 (KR) .................. 10-2010-0117373

(51) Int. Cl.
*C12N 1/12* (2006.01)
(52) U.S. Cl.
USPC ....................................... 435/134; 435/257.1
(58) Field of Classification Search
USPC ............................................ 435/134, 257.1
See application file for complete search history.

(56) References Cited

U.S. PATENT DOCUMENTS

| 2005/0019880 A1 | 1/2005 | Raghukumar et al. |
| 2008/0009045 A1 | 1/2008 | Komazawa et al. |
| 2008/0032361 A1 | 2/2008 | Bailey et al. |
| 2009/0209014 A1 | 8/2009 | Chi et al. |

FOREIGN PATENT DOCUMENTS

| KR | 10-2008-0087820 A | 10/2008 |
| KR | 10-2009-0064603 A | 6/2009 |

OTHER PUBLICATIONS

"*Aurantiochytrium* sp. BL10 18s ribosomal RNA gene, partial sequence", "GenBank: Accession No. FJ821477.1", Mar. 22, 2010.
Kumon, Y., et al, "A New Labyrinthulid Isolate That Produces Only Docosahexaenoic Acid", "Marine Biotechnology", Dec. 28, 2005, pp. 170-177, vol. 8.
Yang, H., et al., "Isolation and Characterization of Taiwanese Heterotrophic Microalgae: Screening of Strains for Docosahexaenoic Acid (DHA) Production", "Mar Biotechnol", Jul. 16, 2009, pp. 173-185, vol. 12.

*Primary Examiner* — Tekchand Saidha
*Assistant Examiner* — Rama P Ramanujam
(74) *Attorney, Agent, or Firm* — Hultquist, PLLC; Steven J. Hultquist (57) ABSTRACT

The present invention relates to novel thraustochytrid-like microalgae having the ability to produce bio-oil, and a method of producing bio-oil using the same. The microalgae of the invention accumulate bio-oil at a high ratio in the cells when being cultured in glucose-containing medium, and thus can produce bio-oil in a high yield. Also, the microalgae can produce bio-oil using bean powder as a nitrogen source, and a product obtained by culturing edible bean powder as medium can be used as a raw material for producing food and feed. Also, the microalgae can produce bio-oil using non-food cellulosic biomass as a carbon source. Moreover, the use of non-food cellulosic biomass for production of bio-oil can overcome the factors limiting the development of bio-oil, including the unstable supply of food resources and an increase in the cost of raw materials, and can improve the commercial competitiveness of microbial fermentation oil.

17 Claims, 6 Drawing Sheets

SEQUENCE LISTING

<160> NUMBER OF SEQ ID NOS: 3

<210> SEQ ID NO 1
<211> LENGTH: 1779
<212> TYPE: DNA
<213> ORGANISM: Thraustochytrid KRS101

<400> SEQUENCE: 1

```
tacctggttg atcctgccag tagtcatatg ctcgtctcaa agattaagcc atgcatgtgt      60
aagtataagc gattgtactg tgagactgcg aacggctcat tatatcagta ataatttctt     120
cggtagtttc ttttatatgg atacctgcag taattctgga aataatacat gctgtaagag     180
ccctgtatgg ggctgcactt attagattga agccgatttt attggtgaat catgataatt     240
gagcagattg acattttgt cgatgaatcg tttgagtttc tgccccatca gttgtcgacg      300
gtagtgtatt ggactacggt gactataacg ggtgacggag agttagggct cgactccgga     360
gagggagcct gagagacggc taccatatcc aaggatagca gcaggcgcgt aaattaccca     420
ctgtggactc cacgaggtag tgacgagaaa tatcgatgcg aagcgtgtat gcgttttgct     480
atcggaatga gagcaatgta aaaccctcat cgaggatcaa ctggagggca agtctggtgc     540
cagcagccgc ggtaattcca gctccagaag catatgctaa agttgttgca gttaaaaagc     600
tcgtagttga atttctggca tgggcgaccg gtgctttccc tgaatgggga ttgattgtct     660
gtgttgcctt ggccatcttt ctcatgctgt tattggtatg agatctttca ctgtaatcaa     720
agcagagtgt tccaagcagg tcgtatgacc ggtatgttta ttatgggatg ataagatagg     780
acttgggtgc tattttgttg gtttgcacgc ctgagtaatg gttaatagga acagttgggg     840
gtattcgtat ttaggagcta gaggtgaaat tcttggattt ccgaaagacg aactagagcg     900
aaggcattta ccaagcatgt tttcattaat caagaacgaa agtctgggga tcgaagatga     960
ttagatacca tcgtagtcta gaccgtaaac gatgccgact tgcgattgtt gggtgcttta    1020
ttaatgggcc tcagcagcag cacatgagaa atcaaagtct tgggttccg gggggagtat     1080 ggtcgcaagg ctgaaactta aaggaattga cggaagggca ccaccaggag tggagcctgc    1140
ggcttaattt gactcaacac gggaaaactt accaggtcca gacataggta ggattgacag    1200
attgagagct ctttcatgat tctatgggtg gtggtgcatg gccgttctta gttggtggag    1260
tgatttgtct ggttaattcc gttaacgaac gagacctcgg cctactaaat agtgcgtggt    1320
atggcaacat agtacgtttt taacttctta gagggacatg tccggtttac gggcaggaag    1380
ttcgaggcaa taacaggtct gtgatgccct tagatgttct gggccgcacg cgcgctacac    1440
tgatgggttc atcgggtttt aattctgatt tttggaattg agtgcttggt cggaaggcct    1500
ggctaatcct tggaacgctc atcgtgctgg ggctagattt ttgcaattat taatctccaa    1560
cgaggaattc ctagtaaacg caagtcatca gcttgcattg aatacgtccc tgcccttgt     1620 acacaccgcc cgtcgcacct accgattgaa cggtccgatg aaaccatggg atgtttctgt    1680
ttggattaat ttttggacag aggcagaact cgggtgaatc ttattgttta gaggaaggtg    1740
aagtcgtaac aaggtttccg taggtgaacc tgcggaagg                           1779
```

```
-continued

<210> SEQ ID NO 2
<211> LENGTH: 14
<212> TYPE: DNA
<213> ORGANISM: Artificial
<220> FEATURE:
<223> OTHER INFORMATION: primer

<400> SEQUENCE: 2
atgaacatca aaaa                                                     14

<210> SEQ ID NO 3
<211> LENGTH: 14
<212> TYPE: DNA
<213> ORGANISM: Artificial
<220> FEATURE:
<223> OTHER INFORMATION: primer

<400> SEQUENCE: 3
atgaacatca aaaa                                                     14
```

THRAUSTOCHYTRID-BASED MICROALGAE, AND METHOD FOR PREPARING BIO-OIL BY USING SAME

TECHNICAL FIELD

The present invention relates to novel thraustochytrid-like microalgae having the ability to produce bio-oil and a method of producing bio-oil using the same.

BACKGROUND ART

Biodiesel which is produced from the oil of oily plants such as rape seed, soybean and palm is typical biodiesel which has already been commercialized, and the production thereof is increasing rapidly worldwide. However, because raw material crops for producing biodiesel are expensive, biodiesel is disadvantageous in terms of production costs and less competitive compared to crude oil-derived diesel. Thus, despite its various advantages in terms of environment and agricultural economy, biodiesel appears to have no commercial competitiveness, if there is no tax reduction. The increase in raw oil prices by energy exhaustion is expected to give commercial competitiveness to biodiesel, but a sudden rise in the price of raw crops by a recent increase in the production of biodiesel becomes a new factor that reduces the competitiveness of biodiesel.

Moreover, photosynthetic oil from oily plants and photosynthetic microalgae, which is the major source of bio-oil for producing biodiesel, has important advantages in that it uses sunlight and recycles carbon dioxide, but it is disadvantageously influenced by various factors, including time, space, seasons and climate. Also, an increase in the use of biodiesel which is produced from photosynthetic oil can cause food shortages and new environmental problems by the mass cultivation of raw material crops, and thus there are doubts on the effectiveness of biodiesel from photosynthetic oil.

For these reasons, the fermentation of organotrophic microorganisms has received attention as a method for the mass production of bio-oil. Typical microorganisms that produce oil include *Chlorella protothecoides, Yarrowia lipolytica, Rhodosporidium toruloides, Rhodotorula glutinis* and the like, and studies on processes for the fermentation thereof have been actively conducted.

Among these oily microorganisms, microalgae belonging to the thraustochytrid family are oily microorganisms capable of producing bio-oil, which contains polyunsaturated fatty acids such as DHA (docosahexaenoic acid), in an amount of up to 70% of the dry cell weight. DHA, a fatty acid essential for brains, ocular tissue and nervous systems, is known to play an important role in the sight of infants and the development of motor nerves. In addition, it was reported that the amount of DHA is significantly reduced in the brain of dementia patients, and DHA has been reported to have various new functions, such as inhibition of age-related macular degeneration. Despite such useful physiological functions, the human body cannot self-synthesize a sufficient amount of DHA. Thus, DHA is recognized as an essential nutrient to be supplied from the outside, many global organizations, including the World Health Organization, recommend that 1 g or more per day of DHA be taken. Thus, DHA is being commercialized as various products, including health functional foods, and the utility thereof as a raw material for medical drugs is high, indicating that DHA has a very high commercial value. Thus, oil from the fermentation of microalgae belonging to the thraustochytrid family can provide a connection between high-value-added industries utilizing DHA and the biodiesel industry, thereby providing commercial competitiveness to biodiesel, unlike general microbial oil or photosynthetic oil.

However, the most important factor for ensuring the commercial competitiveness of microbial fermentation oil as a raw material for biodiesel is the use of industrial waste, waste resources and surplus biomass as nutrient sources, and ultimately the use of abundant non-edible cellulosic biomass. Examples of non-food cellulosic biomass resources include woody biomass, agricultural byproducts, urban waste and so on.

A number of methods of producing DHA (docosahexaenoic acid) using microorganisms of the thraustochytrid family have been reported. Such methods are mainly methods of producing DNA by culturing microorganisms of the thraustochytrid family in media containing glucose as a carbon source (Korean Patent Laid-Open Publication No. 2008-0087820, Korean Patent Laid-Open Publication No 2009-0064603, US Patent Publication No. 20080009045, and US Patent Publication No. 20050019880). However, there has been no report on a method of producing bio-oil using non-food cellulosic biomass that is the next-generation biomass resources.

Accordingly, the present inventors have made extensive efforts to develop a method of producing DHA in a high yield using microalgae and, as a result, have found that novel thraustochytrid-like microalgae isolated from soil in a mangrove area in Malaysia contain a high concentration of DHA and that bio-oil containing DHA is produced when the novel microalgae are cultured using bean powder or cellulosic biomass as a nutrient source, thereby completing the present invention.

DISCLOSURE OF INVENTION

Technical Problem

It is an object of the present invention to provide a novel microalgal strain that produces bio-oil in a high yield.

Another object of the present invention is to provide a method of producing bio-oil using the novel microalgal strain.

Technical Solution

To achieve the above objects, the present invention provides thraustochytrid-like microalgae KRS101 (KCTC11686BP) having the ability to produce bio-oil.

The present invention also provides a method for producing bio-oil, the method comprising the steps of: (a) culturing thraustochytrid-like microalgae KRS101 (KCTC11686BP) to produce bio-oil; and (b) recovering the produced bio-oil.

The present invention also provides a method for producing bio-oil, the method comprising the steps of: (a) culturing thraustochytrid-like microalgae KRS101 (KCTC11686BP) in a bean powder-containing medium to produce bio-oil; and (b) recovering the produced bio-oil.

The present invention also provides a method for producing bio-oil, the method comprising the steps of: (a) culturing thraustochytrid-like microalgae KRS101 (KCTC11686BP) in a cellulosic biomass-containing medium to produce bio-oil; and (b) recovering the produced bio-oil.

Other features and embodiments of the present invention will be more apparent from the following detailed descriptions and the appended claims

DETAILED DESCRIPTION OF THE INVENTION AND BEST MODE FOR CARRYING OUT THE INVENTION

Unless defined otherwise, all technical and scientific terms used herein have the same meaning as commonly understood by one of ordinary skill in the art to which the invention pertains. Generally, the nomenclature used herein are well known and are commonly employed in the art.

In one aspect, the present invention is directed to thraustochytrid-like microalgae KRS101 (KCTC11686BP) having the ability to produce bio-oil.

Thraustochytrid-like microalgae KRS101 according to the present invention were isolated from a leaf/soil sample in a mangrove area in Malaysia and were obtained by culturing the sample in B1 medium (solution of 1 g/L yeast extract, 1 g/L peptone and 10 g/L agar in 1 L of natural seawater containing 300 mg/L penicillin G and 500 mg/L streptomycin sulfate) for isolation of thraustochytrid microalgae, isolating the culture and isolating a strain that formed zoospores which are the typical characteristics of thraustochytrid microalgae.

The results of 18S rRNA sequencing for biological identification of thraustochytrid-like microalgae KRS101 (KCTC11686BP) revealed that the microalgae have a 18S rRNA nucleotide sequence of SEQ ID NO: 1.

In the present invention, bio-oil which is produced by the microalgae KRS101 may comprise an unsaturated fatty acid, and the unsaturated fatty acid may be docosahexaenoic acid (DHA).

The ratio of the content of docosahexaenoic acid (DHA) to the total content of fatty acids contained in the microalgae KRS101 may be 40% or more, preferably 45% or more, and more preferably 49% or more.

In one example of the present invention, it was shown that the microalgal strain KRS101 according to the present invention contains a high concentration of highly unsaturated fatty acids, and particularly the content of DHA reaches 49.5% of the total fatty acid content.

In another example of the present invention, the microalgal strain KRS101 of the present invention was cultured in basal media containing various concentrations of glucose as a single carbon source. As a result, it was shown that the growth of the microalgal cells was the highest at a glucose concentration of 60 g/L (dry cell weight: 9.09 g/L), and the content of oil was 45% of the dry cell weight, and the content of DHA was 41.22% of the total fatty acid content.

In still another example of the present invention, the microalgal strain KRS101 of the present invention was cultured in basal media containing various concentrations of a yeast extract as a single nitrogen source. As a result, it was shown that the growth of the microalgal cells became higher with an increase in the concentration of the yeast extract, whereas the content of oil increased with a decrease in the concentration of the yeast extract. In addition, the content of DHA slightly decreased with a decrease in the concentration of the yeast extract. The effect of the concentration of seawater salt was examined and, as a result, it was shown that the growth of microalgal cells and the content of oil and DHA increased with a decrease in the concentration of seawater salt.

In still another example of the present invention, the microalgal strain KRS101 of the present invention was cultured in media containing 60 g/L fructose, arabinose, xylose, lactose, maltose, sucrose, glycerol or crude glycerol in place of glucose as a carbon source. As a result, it was shown that the growth of the microalgal cells slightly decreased, but was still possible, and particularly, the use of the biodiesel waste crude glycerol as the carbon source showed an increase in the growth of the microalgal cells compared to the use of pure glycerol.

In still another example of the present invention, the microalgal strain KRS101 of the present invention was cultured in a medium containing 10 g/L of corn steep liquor, a beef extract, a malt extract, peptone or tryptone as a yeast extract in place of an organic nitrogen source. As a result, it was shown that the growth of the microalgal cells was possible, and particularly the use of corn steep liquor showed microalgal cell growth similar to the use of the yeast extract. Further, the effects of various inorganic nitrogen salts were examined using media containing ammonium acetate (2.34 g/L), ammonium nitrate (1.22 g/L), ammonium sulfate (2.0 g/L), sodium nitrate (2.58 g/L) or urea (0.9 g/L), and as a result, it was shown that the growth of the microalgal cells was the highest in the medium containing ammonium acetate or urea. Meanwhile, the effects of non-chlorine salts were examined using media containing sodium acetate (15.48 g/L), sodium bicarbonate (15.86 g/L), sodium carbonate (10.0 g/L), sodium citrate (27.8 g/L), sodium nitrate (16.0 g/L) and sodium sulfate (13.4 g/L), and as a result, it was shown that the KRS101 strain showed good cell growth in all the media.

In another aspect, the present invention is directed to a method for producing bio-oil, the method comprising the steps of: (a) culturing thraustochytrid-like microalgae KRS101 (KCTC11686BP) to produce bio-oil; and (b) recovering the produced bio-oil.

In the present invention, the culture may be fed-batch culture or batch culture.

In one example of the present invention, the microalgal strain KRS101 was batch-cultured in media containing 60 g/L glucose, 10 g/L corn steep liquor, 5 g/L ammonium acetate, 3 g/L $KH_2PO_4$ and 15 g/L seawater salt. As a result, it was shown that the strain completely consumed glucose at 72 hours of culture, and at that time, the dry cell weight, the oil content and the DHA content were 24.8 g/L, 31.2% and 36.7%, respectively, and the amounts of production of oil and DHA were 7.8 g/L and 2.9 g/L, respectively. Meanwhile, the microalgal strain KRS101 was fed-batch-cultured under the same conditions as above, and as a result, it was shown that the highest cell growth appeared at 60 hours of culture, and at that time, the dry cell weight, the oil content and the DHA content were 50.2 g/L, 43.5% and 40.3%, respectively, and the amounts of production of oil and DHA were 21.9 g/L and 8.8 g/L, respectively.

In still another aspect, the present invention is directed to a method for producing bio-oil, the method comprising the steps of: (a) culturing thraustochytrid-like microalgae KRS101 (KCTC11686BP) in a bean powder-containing medium to produce bio-oil; and (b) recovering the produced bio-oil.

In the present invention, the bean powder may be used as a single nitrogen source.

In the present invention, bio-oil which is produced by the KRS101 strain may be an unsaturated fatty acid, and the unsaturated fatty acid may be docosahexaenoic acid (DHA).

In addition, the culture may be fed-batch culture or batch culture.

In one example of the present invention, the microalgal strain KRS101 showed high cell growth rate in media containing bean powder as a nitrogen source, and the productivity of bio-oil containing DHA was also high in the media.

In still another aspect, the present invention is directed to a method for producing bio-oil, the method comprising the steps of: (a) culturing thraustochytrid-like microalgae KRS101 (KCTC11686BP) in a cellulosic biomass-containing medium to produce bio-oil; and (b) recovering the produced bio-oil.

In the present invention, the medium may contain cellulosic biomass as a single carbon source, and the cellulosic biomass may be selected from the group consisting of carboxymethylcellulose, cellobiose, and palm oil byproducts.

The thraustochytrid-like microalgae may be KRS101 (KCTC11686BP).

Moreover, bio-oil which is produced by the thraustochytrid-like microalgae may comprise an unsaturated fatty acid, and the unsaturated fatty acid may be docosahexaenoic acid (DHA).

In the present invention, the culture may be fed-batch culture or batch culture.

In one example of the present invention, the microalgal strain KRS101 was cultured using the cellulosic biomass carboxymethylcellulose, cellobiose or a palm oil byproduct as a carbon source, and as a result, it was shown that the proliferation of the KRS101 strain was possible. In addition, the contents of oil and DHA were measured using a modified Bligh-Dyer method, and as a result, it was shown that, at 72 hours of culture, the amounts of production of oil and DNA when carboxymethylcellulose was used were 0.3 g/L and 0.18 g/L (60.7% TFA), and the amounts of production of oil and DNA when cellobiose was used were 0.4 g/L and 0.24 g/L (59.8% TFA), respectively. In addition, the amounts of production of oil and DNA when the palm oil byproduct was used were 0.3 g/L and 0.16 g/L (54.3% TFA).

In another example of the present invention, the activities of the CMCase and Cellobiosidase enzymes believed to be involved in the use of cellulosic biomass in the culture broth of the microalgae KRS101 were examined. As a result, it was shown that the activities of CMCase and cellobiosidase enzymes were detected in the culture broth of the microalgae KRS101, even though these activities varied depending on the kind of cellulosic nutrient source.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1

Isolation and Identification of Novel Oily Microalgae Containing DHA

Figure 1:
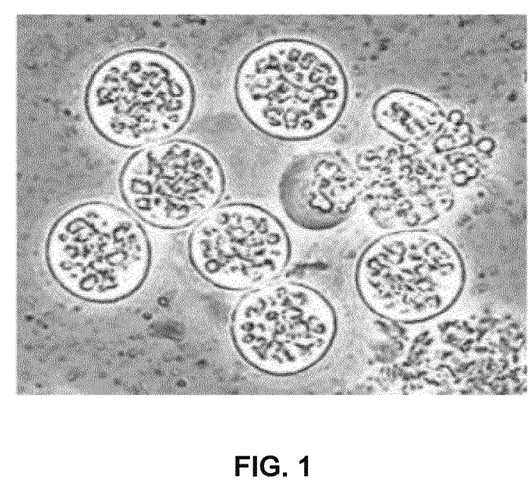
FIG. 1 is a micrograph of novel thraustochytrid-like microalgae KRS101.

A leaf/soil sample was collected in a mangrove area in Malaysia using a 50-ml falcon tube and suspended in 10 ml of saline, after which the suspension was diluted suitably and inoculated in B1 medium (solution of 1 g/L yeast extract, 1 g/L peptone and 10 g/L agar in 1 L of natural seawater containing 300 mg/L penicillin G and 500 mg/L streptomycin sulfate) (Burja et al. 2006) for isolation of thraustochytrid microalgae. The medium was incubated at 28° C. at 200 rpm for 2-4 days, and the obtained colonies were inoculated again in B1 medium. Then, the colonies were observed with a microscope, and 30 colonies were isolated, which formed zoospores which are the typical characteristics of thraustochytrid microalgae (see FIG. 1).

The 30 isolated colonies were cultured in 50 mL of a marine broth (Sigma-Aldrich) (250-mL flask) at 28° C. at 120 rpm for 3 days, and then the cells were collected and dried in a vacuum centrifuge at 60° C. for 12 hours. The dried cells were suspended in 3 ml of 5% methanolic sulfuric acid and incubated at 90° C. for 1 hour, and then the produced fatty acid ester was extracted with 0.6 mL of hexane and analyzed by gas chromatography.

The results of the analysis are shown in Table 1 below. As can be seen therein, the microalgal cells contained a high concentration of highly unsaturated fatty acids, and particularly the content of DNA in the cells reached 49.5% of the total fatty acid content. In addition, the 30 analyzed colonies showed similar fatty acid compositions.

TABLE 1

Fatty acid composition of novel thraustochytrid-like microalgae KRS101

| | Fatty acid composition (% TFA) | | | | | | | | | | |
|---|---|---|---|---|---|---|---|---|---|---|---|
| | 14:0 | 15:0 | 16:1 | 16:0 | 17:0 | 18:3 | 18:2 | 18:1 | 20:5 | 22:5 (n6) | 22:6 | 22:5 (n3) |
| Marine | — | 17.39 | — | 8.89 | 3.1 | — | 0.93 | — | 2.18 | 8.12 | 49.59 | 0.86 |
| Basal | 2.73 | 14.09 | 0.43 | 24.60 | 2.72 | 0.26 | — | 0.91 | 0.48 | 10.00 | 39.49 | 0.35 |

For molecular biological identification of the isolated colonies, 18S rRNA sequencing was performed.

Chromosomal DNA was isolated from one colony using a conventional phenol-chloroform method, and the 18S rRNA gene therefrom was amplified by PCR using the primers 5'-ATGAACATCAAAAA-3' (P1, SEQ ID NO: 2) and 5'-ATGAACATCAAAAA-3'(P2, SEQ ID NO: 3) for amplification of the thraustochytrid microalgae 18S rRNA gene. Specifically, for PCR amplification, a PCR reaction solution (50 μl) containing EF Taq polymerase (Takara) (2.5 U), polymerase buffer, dNTPs (each 1 mM), 1 μl of each primer (100 pmol) and 500 ng of template DNA was prepared and subjected to PCR using a PCR system (Takara, Japan) for 30 cycles, each consisting of 96° C. for 30 sec, 43° C. for 1 min and 72° C. for 3 min. The PCR product was electrophoresed on 1% agarose gel to confirm that a DNA fragment having the expected size was amplified, and it was transformed into *E. coli* DH5α using a pGEM-TEasy vector (Promega, USA). Plasmid DNA was extracted from the transformed recombinant *E. coli* cells (Qiagen, USA) and digested with the restriction enzyme EcoRI to confirm that a DNA fragment having the desired size was cloned, and it was sequenced (SEQ ID NO: 1, GenBank accession number HM126528). The results of analysis of sequence homology indicated that the strain was a novel thraustochytrid-like microalgae strain showing homologies of 99.3% and 98.9% with *Aurantiochytrium mangrovei* and *Aurantiochytrium* sp. BL1, respectively. Thus, the microalgal strain was named "KRS101" and deposited with the Korean Collection for Type Cultures (KCTC), the Korea Research Institute of Bioscience and Biotechnology, on April 2010 under accession number KCTC11686BP.

Figure 2:
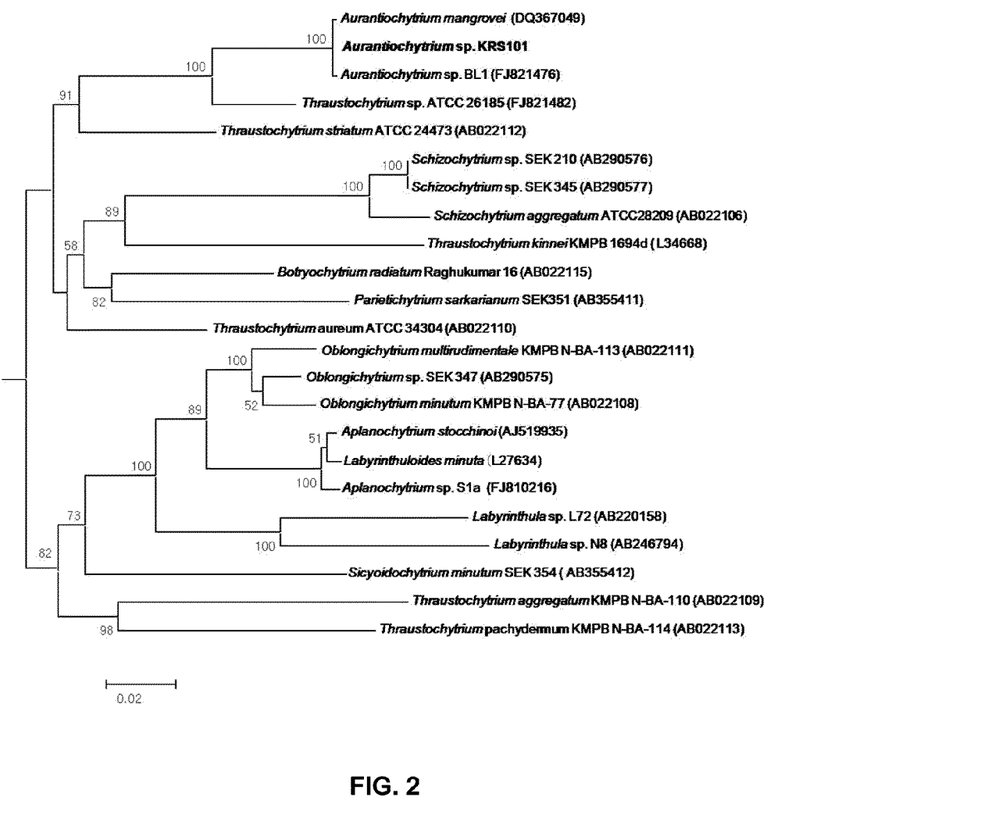
FIG. 2 shows a phylogenetic diagram of novel thraustochytrid-like microalgae KRS101.

FIG. 2 shows a phylogenetic diagram of the novel thraustochytrid-like microalgae KRS101.

Example 2

Analysis of the Cell Growth of Novel Thraustochytrid-like Microalgae KRS101 and the Ability of the Microalgae to Produce DHA-containing Oil The cell growth of novel thraustochytrid-like microalgae KRS101 isolated in Example 1 and the ability of the microalgae to produce DHA-containing oil were examined under the conditions of various nutrient sources.

As a basal medium, a medium containing 60 g/L of the carbon source glucose, 1 g/L of the nitrogen source yeast extract and 6 g/L of artificial seawater salt was used. A single colony was pre-cultured in 15 ml of a basal medium at 28° C. at 120 rpm for 3 days, after which 1 ml of the culture broth was inoculated into media containing various concentrations of a carbon source, a nitrogen source and a seawater salt and was cultured at 28° C. at 120 rpm for 3 days. The cells collected by centrifugation were washed three times with PBS buffer (phosphate buffered saline, pH 7.2) and dried at 60° C. for 12 hours, and the dry cell weight (DCW) was measured.

The content of DHA-containing oil was analyzed using a modified Bligh-Dyer method (Burja et al., 2007). Specifically, 6.25 mL of chloroform, 12.5 mL of methanol and 5 mL of 50 mM $K_2HPO_4$ buffer (pH 7.4) were added to 125 mg of the dry cells which were then incubated at 28° C. at 200 rpm for 1 hours, after which 6.25 mL of chloroform and 6.25 mL of $K_2HPO_4$ buffer were added thereto, and the cell solution was shaken about 30 times and allowed to stand for 30 minutes so that it was separated into a water layer and an organic solvent layer containing oil. The chloroform layer was carefully transferred into an aluminum dish which had been previously weighed, and then it was dried at 80° C. for 30 minutes, after which the weight of the oil was measured. The total oil content was calculated using the following equation:

Total oil content (%)=oil (g)/dry cell weight (100 g)= $(W_L-W_D) \times V_C \times 100 / V_P \times W_S$ $W_L$: weight of aluminum dish;
$W_D$: weight of aluminum dish+lipid;
$V_C$: total volume of chloroform;
$V_P$: volume of chloroform transferred into aluminum dish;
$W_S$: weight of cells used (dry cell weight).

Meanwhile, the content of DNA in the oil was measured by gas chromatography. Specifically, a suitable amount of the dry cells were suspended in 3 ml of 5% methanol-sulfuric acid solution and incubated at 90° C. for 1 hour to produce fatty acid ester, which was then extracted with 0.6 ml of hexane and analyzed by gas chromatography.

The results of the analysis are shown in Table 1 above. As can be seen therein, when the novel microalgal strain KRS101 was cultured in the basal medium, the composition of fatty acids slightly changed compared to when the strain was cultured in the marine broth, but highly unsaturated fatty acids, including DHA, were produced at high concentrations.

The novel microalgal strain KRS101 was cultured in basal media containing various concentrations of glucose as a single carbon source. As a result, as can be seen in Table 2 below, the strain showed the highest cell growth at a glucose concentration of 60 g/L (dry cell weight: 9.09 g/L), and at that concentration, the content of oil was 45% of the dry cell weight, and the content of DHA was 41.22% of the total fatty acid content.

TABLE 2

Effects of glucose concentration on the cell growth and oil and DHA contents of novel thraustochytrid-like microalgae KRS101

| Concentrations (g L⁻¹) | Dry cell weights (g L⁻¹) | Contents of oil (% DCW) | DHA (% TFA) |
|---|---|---|---|
| 5 | 4.49 | 8.50 | 44.08 |
| 20 | 8.22 | 35.85 | 40.13 |
| 40 | 7.38 | 36.75 | 41.19 |
| 60 | 9.09 | 45.00 | 41.22 |
| 100 | 5.57 | 28.10 | 38.76 |
| 160 | 6.19 | 27.45 | 40.57 |

Meanwhile, the novel microalgal strain KRS101 was cultured in basal media containing various concentrations of a yeast extract as a single carbon source. As a result, as can be seen in Table 3 below, the cell growth increased with an increase in the concentration of the yeast extract, whereas the content of oil increased with a decrease in the concentration of the yeast extract and increased to 70% of the highest dry cell weight. On the other hand, the content of DHA in the total fatty acids slightly decreased with a decrease in the concentration of the yeast extract.

TABLE 3

Effects of yeast extract concentration on the cell growth and oil and DHA contents of thraustochytrid-like microalgae KRS101

| Concentrations (g L⁻¹) | Dry cell weights (g L⁻¹) | Contents of oil (% DCW) | DHA (% TFA) |
|---|---|---|---|
| 2 | 6.28 | 70.00 | 32.66 |
| 4 | 6.50 | 53.25 | 35.15 |
| 6 | 6.12 | 51.90 | 39.55 |
| 8 | 7.68 | 48.00 | 38.74 |

Subsequently, the effects of the concentration of seawater salt were examined. As a result, as can be seen in Table 4 below, the cell growth and the contents of oil and DHA decreased with a decrease in the concentration of seawater salt.

TABLE 4

Effects of seawater salt concentration on the cell growth and oil and DHA contents of thraustochytrid-like microalgae KRS101

| Concentrations (g L$^{-1}$) | Dry cell weights (g L$^{-1}$) | Contents of oil (% DCW) | DHA (% TFA) |
| --- | --- | --- | --- |
| 2  | 7.62 | 50.80 | 41.87 |
| 6  | 7.75 | 45.00 | 37.77 |
| 15 | 7.87 | 40.35 | 35.06 |
| 30 | 6.19 | 14.65 | 34.94 |
| 40 | 6.37 | 14.20 | 36.17 |
| 50 | 7.27 | 13.20 | 35.25 |

Example 3

Ability of Thraustochytrid-like Microalgae KRS101 to Use Various Nutrient Sources The ability of thraustochytrid-like microalgae KRS101 to use various nutrient sources was examined. Specifically, the microalgal strain KRS101 was cultured in basal media containing various carbon sources, nitrogen sources or non-chlorine salts in the same manner as described above, and the cell growth and the contents of oil and DHA were examined.

The microalgal strain KRS101 was cultured in media containing 60 g/L of fructose, arabinose, xylose, lactose, maltose, sucrose, glycerol or crude glycerol as a carbon source in place of glucose. As a result, as can be seen in Table 5, the cell growth of the microalgal strain KRS101 was still possible in the media, even though it decreased compared to that in the media containing glucose. Particularly, the use of the biodiesel waste crude glycerol as the carbon source showed higher cell growth than the use of pure glycerol.

TABLE 5

Cell growth and DHA-containing oil production of thraustochytrid-like microalgae KRS101 using various carbon sources

| Carbon sources | Dry cell weights (g L$^{-1}$) | Contents of oil (% DCW) | DHA (% TFA) |
| --- | --- | --- | --- |
| Fructose | 10.15 | 15.30 | 37.25 |
| Arabinose | 3.00 | 8.90 | 43.88 |
| Xylose | 3.38 | 8.50 | 43.90 |
| Lactose | 4.41 | 9.00 | 46.55 |
| Maltose | 4.15 | 6.50 | 52.36 |
| Sucrose | 4.27 | 21.80 | 48.25 |
| Pure glycerol | 5.60 | 9.40 | 37.56 |
| Crude glycerol | 7.32 | 8.50 | 43.38 |

Also, the microalgal strain KRS101 was cultured in media containing 10 g/L of corn steep liquor, a beef extract, a malt extract, peptone or tryptone in place of a yeast extract as an organic nitrogen source. As a result, as can be seen in Table 6 below, the cell growth of the novel microalgal strain KRS101 was possible in the media, and particularly the cell growth in the corn steep liquor was similar to that in the yeast extract. In addition, the effects of various inorganic nitrogen salts were examined using media containing ammonium acetate (2.34 g/L), ammonium nitrate (1.22 g/L), ammonium sulfate (2.0 g/L), sodium nitrate (2.58 g/L) or urea (0.9 g/L). As a result, as can be seen in Table 7 below, the cell growth was the highest in ammonium acetate and urea.

TABLE 6

Cell growth and DHA-containing oil production of thraustochytrid-like microalgae KRS101 using various organic nitrogen sources

| Organic nitrogen sources | Dry cell weights (g L$^{-1}$) | Contents of oil (% DCW) | DHA (% TFA) |
| --- | --- | --- | --- |
| Corn steep liquor | 9.44 | 15.30 | 37.25 |
| Beef extract | 3.00 | 8.90 | 43.88 |
| Malt extract | 3.38 | 8.50 | 43.90 |
| peptone | 4.41 | 9.00 | 46.55 |
| Tryptone | 7.32 | 8.50 | 43.38 |

TABLE 7

Cell growth and DHA-containing oil production of thraustochytrid-like microalgae KRS101 using various inorganic nitrogen sources

| Inorganic nitrogen sources | Dry cell weights (g L$^{-1}$) | Contents of oil (% DCW) | DHA (% TFA) |
| --- | --- | --- | --- |
| Ammonium acetate | 9.52 | 55.40 | 43.00 |
| Ammonium nitrate | 5.99 | 32.10 | 47.06 |
| Ammonium sulfate | 6.04 | 19.80 | 49.34 |
| Sodium nitrate | 6.00 | 63.50 | 28.25 |
| Urea | 10.28 | 57.70 | 29.78 |

Meanwhile, the effects of non-chlorine salts were examined using media containing sodium acetate (15.48 g/L), sodium bicarbonate (15.86 g/L), sodium carbonate (10.0 g/L), sodium citrate (27.8 g/L), sodium nitrate (16.0 g/L) or sodium sulfate (13.4 g/L). As a result, as can be seen in Table 8 below, the novel microalgal strain KRS101 showed good cell growth in all the media.

TABLE 8

Cell growth and DHA-containing oil production of novel thraustochytrid-like microalgae KRS101 using various non-chlorine salts

| Non-chlorine salts | Dry cell weights (g L$^{-1}$) | Contents of oil (% DCW) | DHA (% TFA) |
| --- | --- | --- | --- |
| Sodium acetate | 6.70 | 20.30 | 45.65 |
| Sodium bicarbonate | 6.29 | 4.30 | 4.23 |
| Sodium carbonate | 5.15 | 5.74 | 7.21 |

TABLE 8-continued

Cell growth and DHA-containing oil production of novel thraustochytrid-like microalgae KRS101 using various non-chlorine salts

| Non-chlorine salts | Dry cell weights (g L$^{-1}$) | Contents of oil (% DCW) | DHA (% TFA) |
|---|---|---|---|
| Sodium citrate | 3.20 | 15.80 | 39.19 |
| Sodium nitrate | 7.43 | 29.00 | 28.25 |
| Sodium sulfate | 7.53 | 21.30 | 40.30 |

Example 4

Production of DHA-containing Bio-oil by Culture of Novel Thraustochytrid-like Microalgae KRS101 in Fermenter Based on the above-described results of analysis of nutrient requirements, an optimal medium composition was selected, and the novel microalgal strain KRS101 was cultured in a 5-L fermenter with the selected medium.

Specifically, the strain KRS101 was pre-cultured in a medium containing the selected medium composition (60 g/L glucose, 10 g/L corn steep liquor, 5 g/L ammonium acetate, 3 g/L $KH_2PO_4$ and 15 g/L seawater salt, and the pre-cultured cells were transferred into 3 L of the same medium (5-L jar fermenter) and batch-cultured under the conditions of 28° C., 300 rpm, 3 vvm and pH 7, while the cells were collected at 12-hr intervals and the growth and oil and DHA contents thereof were examined.

Figure 3:
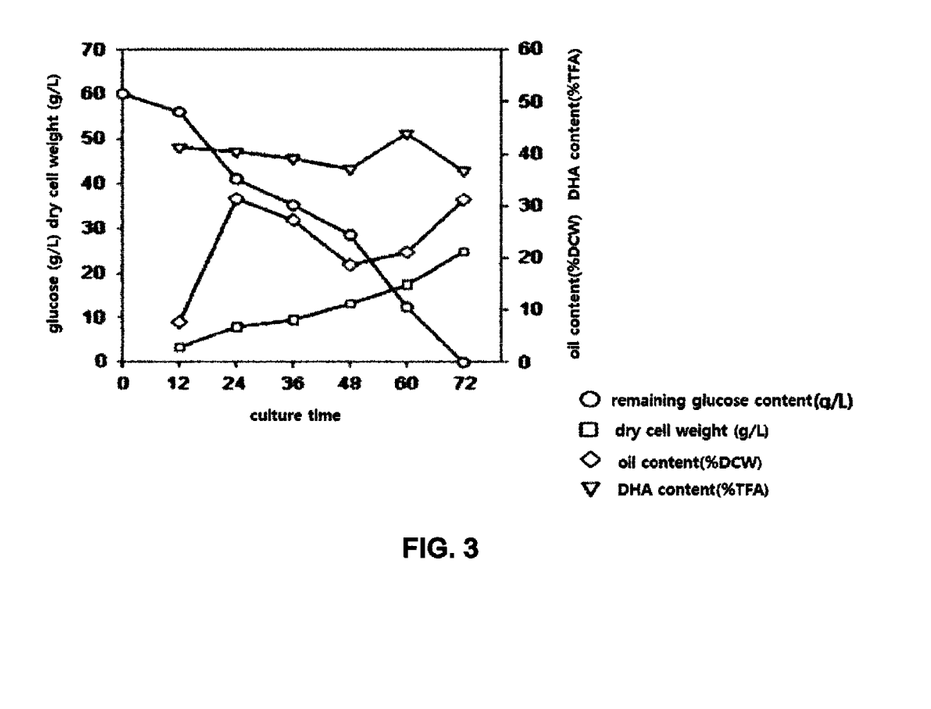
FIG. 3 shows the results of batch culture of novel thraustochytrid-like microalgae KRS101 in a 5-L fermenter.

As a result, as can be seen in FIG. 3, glucose in the medium was completely consumed at 72 hours of culture, and at that time, the dry cell weight and the contents of oil and DNA were 24.8 g/L, 31.2% and 36.7%, respectively, and the amounts of production of oil and DHA were 7.8 g/L and 2.9 g/L, respectively.

Figure 4:
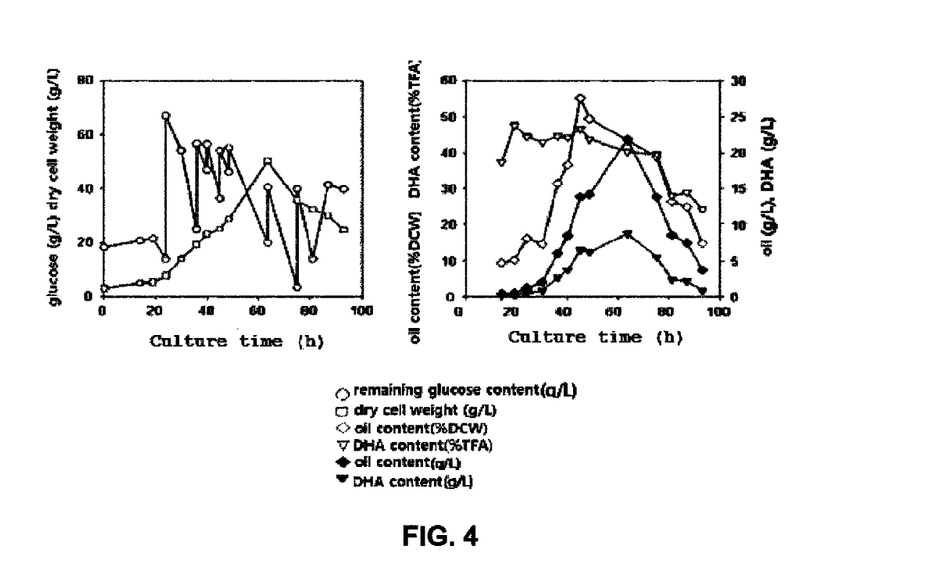
FIG. 4 shows the results of fed-batch culture of novel thraustochytrid-like microalgae KRS101 in a 5-L fermenter.

Meanwhile, the fed-batch culture of the novel microalgal strain KRS101 was carried out under the same conditions as above. As a result, as can be seen in FIG. 4, the highest cell growth appeared at 60 hours of culture, and at that time, the dry cell weight and the contents of oil and DHA were 50.2 g/L, 43.5% and 40.3%, respectively, and the amounts of production of oil and DHA were 21.9 g/L and 8.8 g/L, respectively.

Example 5

Culture of Novel Thraustochytrid-like Microalgae KRS101 in Medium Containing Bean Powder Bean, a source of vegetable protein and fat, has been used as a raw material for foods, such as bean paste, bean-curd, soy sauce and the like. Recently, it was found that bean is rich in isoflavone having various physiological effects, including a cancer prevention effect, and thus it has received a great deal of attention as a health functional food. In addition, bean can be produced in large amounts by mass cultivation, and thus the production cost thereof is low, despite its high nutrient content.

In order to examine whether bean powder having low production costs can be used as a nutrient source in the culture of the novel microalgal strain KRS101, the novel microalgal strain KRS101 was cultured using media (60 g/L glucose, 5 g/L corn steep solid, 5 g/L ammonium acetate, 3 g/L $KH_2PO_4$, and 15 g/L artificial seawater salt) containing various concentrations of bean powder.

Specifically, a single colony of the strain was pre-cultured in 15 ml of a medium (60 g/L glucose, 5 g/L corn steep solid, 5 g/L ammonium acetate, 3 g/L $KH_2PO_4$, and 15 g/L artificial seawater salt) at 28° C. at 120 rpm for 3 days, and 1 ml of the culture broth was inoculated into media containing various concentrations (5 g/L, 10 g/L and 20 g/L) of bean powder and was cultured at 28° C. at 120 rpm for 3 days. Then, the cells were collected and the growth and oil and DHA contents thereof were analyzed. The results of the analysis are shown in Table 9 below. Also, the results of analysis for a control group not inoculated with the microalgae are shown in Table 10 below.

TABLE 9

Analysis results for culture products of novel thraustochytrid-like microalgae KRS101 cultured in media containing bean powder

| Bean powder (g/L) | Dry cell weights (g L$^{-1}$) | Contents of oil (% DCW) | Fatty acid compositions(% TFA) | | | | | | | | | |
|---|---|---|---|---|---|---|---|---|---|---|---|---|
| | | | 14:0 | 15:0 | 16:0 | 18:0 | 18:1 | 18:2 | 20:5 | 22:6 (n6) | 22:6 (n3) | 22:5 (n3) |
| 0 | 29.49 | 22.66 | 3.75 | 0.90 | 44.12 | 0.76 | nd | 0.33 | 1.10 | 6.17 | 32.38 | 1.54 |
| 5 | 31.21 | 24.94 | 3.74 | 0.90 | 42.12 | 1.36 | 4.97 | 6.25 | 1.01 | 5.76 | 29.83 | 1.48 |
| 10 | 35.28 | 25.32 | 3.58 | 0.83 | 41.37 | 2.04 | 7.77 | 9.43 | 1.18 | 4.73 | 26.61 | nd |
| 20 | 41.24 | 27.22 | 2.89 | 0.63 | 37.72 | 2.86 | 11.33 | 13.47 | 1.06 | 3.83 | 19.47 | nd |

20:5, EPA;
22:6 (n6), DPA;
22:6 (n3), DHA;
22:5 (n3), DPA.
nd, not detected

TABLE 10

Component analysis results for bean powder basal media not inoculated with microalgae

| Bean powder (g/L) | Dry cell weights (g L$^{-1}$) | Contents of oil (% DCW) | 14:0 | 15:0 | 16:0 | 18:0 | 18:1 | 18:2 | 20:5 | 22:6 (n6) | 22:6 (n3) | 22:5 (n3) |
|---|---|---|---|---|---|---|---|---|---|---|---|---|
| | | | | | Fatty acid compositions (% TFA) | | | | | | | |
| 5 | 2.82 | 25.10 | nd | nd | 11.20 | 4.04 | 29.85 | 54.25 | nd | nd | nd | nd |
| 10 | 5.35 | 24.76 | nd | nd | 11.50 | 3.76 | 28.66 | 55.28 | nd | nd | nd | nd |
| 20 | 12.70 | 24.16 | nd | nd | 12:08 | 3.60 | 25.21 | 27.60 | nd | nd | nd | nd |

20:5, EPA;
22:6 (n6), DPA;
22:6 (n3), DHA;
22:5 (n3), DPA.
nd, not detected

Based on the above-described results, the novel microalgal strain KRS101 was cultured in media containing bean powder in place of a carbon or nitrogen source.

Specifically, in order to examine whether bean powder can be used as a carbon source, the novel microalgal strain KRS101 was cultured in glucose (carbon source)-free media containing various concentrations (5 g/L, 10 g/L and 20 g/L) of bean powder in the same manner as described above. Then, the cells were collected and the growth and oil and DHA contents thereof were analyzed.

As a result, as can be seen in Table 11 below, the cell growth of the novel microalgal strain KRS101 significantly decreased, suggesting that bean powder is not suitable as a carbon source.

Meanwhile, in order to examine whether powder can be used as an organic nitrogen source, the novel microalgal strain KRS101 was cultured in corn steep solid (organic nitrogen source)-free media containing various concentrations (5 g/L, 10 g/L and 20 g/L) in the same manner as described above. Then, the cells were collected and the growth and oil and DHA contents thereof were analyzed.

As a result, as can be seen in Table 12 below, the novel microalgal strain KRS101 showed very high cell growth, suggesting that bean powder can be used as an effective nitrogen source. The DHA content in Table 12 is expressed as the DHA content (%) of the total fatty acid. As the content of the bean powder increased, the concentrations of fatty acids other than DHA in the bean powder increased, so that the DHA content (%) of the total fatty acid gradually decreased.

TABLE 11

Analysis results for culture products of novel thraustochytrid-like microalgae KRS101 cultured in media containing bean powder in place of glucose as carbon source

| Bean powder (g/L) | Dry cell weights (g L$^{-1}$) | Contents of oil (% DCW) | 14:0 | 15:0 | 16:0 | 18:0 | 18:1 | 18:2 | 20:5 | 22:6 (n6) | 22:6 (n3) | 22:5 (n3) |
|---|---|---|---|---|---|---|---|---|---|---|---|---|
| | | | | | Fatty acid compositions (% TFA) | | | | | | | |
| 0 | 6.20 | 3.96 | 0.94 | 1.21 | 18.32 | 8:36 | 4.64 | 1.47 | 2.54 | 11.44 | 47.34 | 2.41 |
| 5 | 8.24 | 3.94 | 3.74 | 0.56 | 16.72 | 23.75 | 20.59 | 4.53 | 1.13 | 5.80 | 21.46 | 1.16 |
| 10 | 10.34 | 12.59 | nd | 0.36 | 15.56 | 22.66 | 21.19 | 7.91 | 1.36 | 5.27 | 18.58 | 1.24 |
| 20 | 16.54 | 6.81 | nd | nd | 16.36 | 23.61 | 22.04 | 6.17 | 1.74 | 4.84 | 18.70 | 4.28 |

20:5, EPA;
22:6 (n6), DPA;
22:6 (n3), DHA;
22:5 (n3), DPA.
nd, not detected

TABLE 12

Analysis results for culture products of novel thraustochytrid-like microalgae KRS101 cultured in media containing bean powder as nitrogen source

| Bean powder (g/L) | Dry cell weights (g L$^{-1}$) | Contents of oil (% DCW) | 14:0 | 15:0 | 16:0 | 18:0 | 18:1 | 18:2 | 20:5 | 22:6 (n6) | 22:6 (n3) | 22:5 (n3) |
|---|---|---|---|---|---|---|---|---|---|---|---|---|
| | | | | | Fatty acid compositions (% TFA) | | | | | | | |
| 0 | 2.57 | 6.71 | 1.30 | 4.04 | 31.51 | nd | nd | 1.40 | 3.24 | 10.92 | 44.86 | 1.39 |
| 5 | 29.80 | 27.21 | 2.01 | 0.46 | 35.35 | 7.76 | 6.83 | 1.76 | 1.42 | 6.35 | 30.68 | 1.16 |

TABLE 12-continued

Analysis results for culture products of novel thraustochytrid-like microalgae KRS101 cultured in media containing bean powder as nitrogen source

| Bean powder (g/L) | Dry cell weights (g L$^{-1}$) | Contents of oil (% DCW) | Fatty acid compositions (% TFA) | | | | | | | | | |
|---|---|---|---|---|---|---|---|---|---|---|---|---|
| | | | 14:0 | 15:0 | 16:0 | 18:0 | 18:1 | 18:2 | 20:5 | 22:6 (n6) | 22:6 (n3) | 22:5 (n3) |
| 10 | 32.02 | 32.26 | 3.09 | 0.64 | 42.07 | 9.95 | 8.16 | 2.66 | 0.94 | 4.92 | 24.03 | nd |
| 20 | 42.99 | 35.20 | 2.48 | nd | 34.02 | 9.55 | 7.80 | 2.88 | 0.72 | 2.94 | 15.79 | nd |

20:5, EPA;
22:6 (n6), DPA;
22:6 (n3), DHA;
22:5 (n3), DPA.
nd, not detected

Example 6

Figure 5:
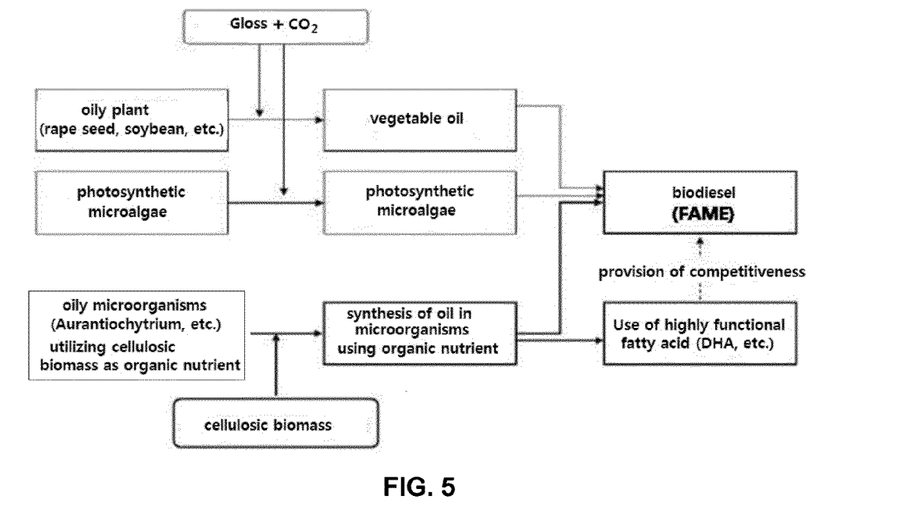
FIG. 5 is a schematic diagram showing the production of bio-oil by novel thraustochytrid-like microalgae KRS101 using cellulosic biomass as a nutrient source and the use thereof.

Culture of Novel Thraustochytrid-like Microalgae KRS101 Using Cellulosic Biomass as Nutrient Source The most important factor for ensuring the commercial competitiveness of microbial fermentation oil as a raw material for biodiesel is the use of industrial waste, waste resources and surplus biomass as nutrient sources, and ultimately the use of abundant non-edible cellulosic biomass (see FIG. 5).

Thus, in order to examine whether cellulosic biomass can be used as a nutrient source in the culture of the novel microalgal strain KRS101, a single colony of the strain was inoculated into a basal medium containing 60 g/L carbon source glucose, 1 g/L nitrogen source yeast extract and 6 g/L artificial seawater salt and was pre-cultured at 28° C. at 120 rpm for 3 days. Then, 1 ml of the pre-culture broth was inoculated into each of a basal medium containing 0.5% (w/v) of carboxymethylcellulose (CMC) in place of glucose as a carbon source, a basal medium containing 0.5% (w/v) of cellobiose as a carbon source, and a basal medium containing 0.5% (w/v) of a palm oil byproduct (empty fruit bunch (EFB)), and was cultured at 28° C. at 120 rpm, while the growth of the cells was analyzed by measuring the absorbance (optical density (OD)) at 600 nm.

In the case in which a palm oil byproduct was used as industrially usable cellulosic biomass resources, the palm oil byproduct was crushed to a size of about 1-2 mm, dipped in 0.5M NaOH solution for 4 hours, autoclaved at 121° C. and 15 psi for 15 minutes, washed with water to remove NaOH, and dried. The palm oil byproduct thus pretreated was used in the preparation of media.

Figure 6:
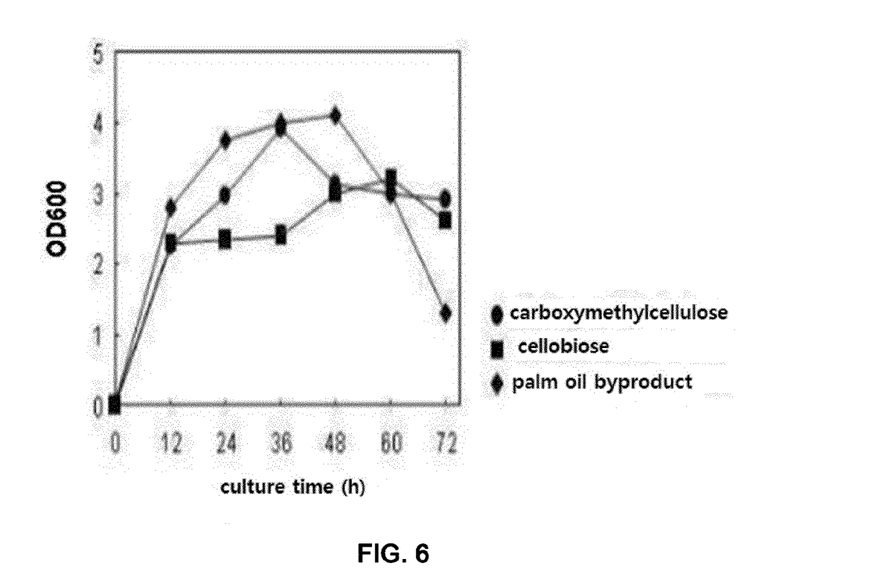
FIG. 6 is a graph showing the proliferation of novel thraustochytrid-like microalgae KRS101 using cellulosic biomass as a nutrient source.
Figure 7:
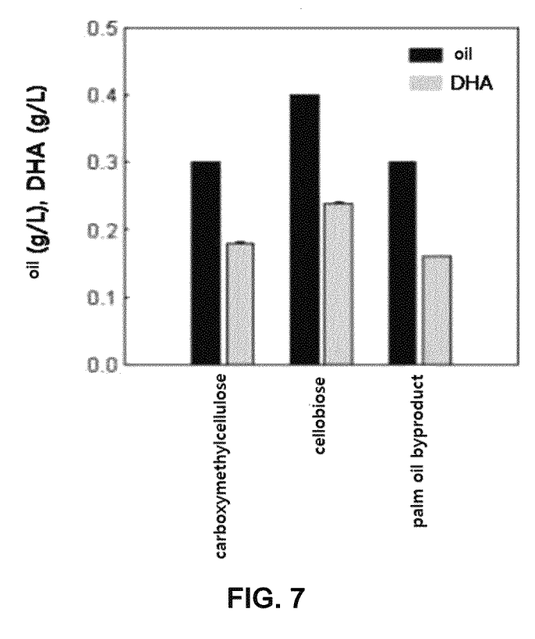
FIG. 7 is a graph showing the amounts of the oil and DNA produced by culturing novel thraustochytrid-like microalgae KRS101 using cellulosic biomass as a nutrient source.

As a result, as can be seen in FIG. 6, the use of carboxymethylcellulose, cellobiose and palm oil byproducts as nutrient sources enabled the proliferation of the novel microalgal strain KRS101. In addition, as can be seen in FIG. 7, at 72 hours of culture, the amounts of production of oil and DHA when carboxymethylcellulose was used were 0.3 g/L and 0.18 g/L (60.7% TFA), respectively, and the amounts of production of oil and DHA when cellobiose was used were 0.4 g/L and 0.24 g/L (59.8% TFA), respectively. Also, the amounts of production of oil and DHA when the palm oil byproduct was used were 0.3 g/L and 0.16 g/L (54.3% TFA).

It has been known that microalgae of the thraustochytrid family have no cellulase activity (Taoka et al. *Biosci Biotechnol Biochem.*, 73:180, 2009), but it was recently found that thraustochytrid microalgae (*Aplanochytrium, Botryochytrium, Oblongichytrium, Parietichytrium, Schizochytrium, Sicyoidochytrium, Thraustochytrium* and *Ulkenia*) other than *Aurantiochytrium* sp. have CMCase activity (Nagano et al. *Mar Biotechnol*, 2010).

Thus, the activities of the cellulases (CMCase and cellobiosidase) believed to be involved in the use of cellulosic biomass in the novel microalgal strain KRS101 were analyzed.

To examine the activity of CMCase, 0.2 ml of a sample (cell lysate or culture supernatant) was mixed with 0.8 ml of 10 mM Tris-HCl buffer (pH 6.5) containing 1% (w/v) CMC, and the mixture was incubated at 60° C. for 2 hours. The concentration of released reducing sugar was measured using the DNS (3,5-dinitrosalicylic acid) method, and one enzyme activity unit was defined as activity per mg protein.

Figure 8:
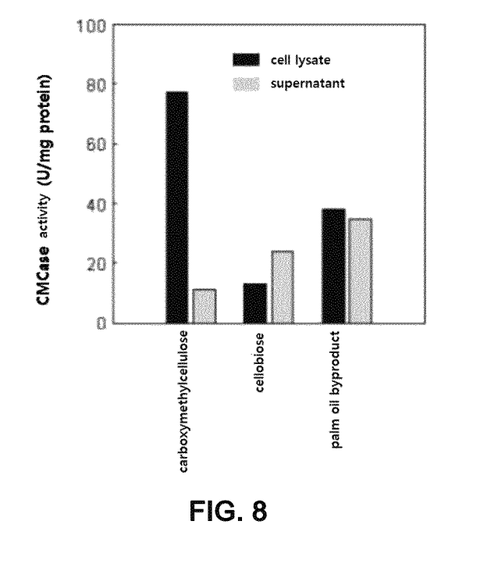
FIG. 8 is a graph showing the CMCase activity of a culture of novel thraustochytrid-like microalgae KRS101 cultured using cellulosic biomass as a nutrient source.

As a result, as can be seen in FIG. 8, the activity of CMCase was detected in the culture broth of the novel microalgal strain KRS101, even though it varied depending on the kind of cellulosic nutrient source. In addition, the use of CMC as the substrate showed the highest enzymatic activity.

To measure the activity of cellobiosidase, 0.2 ml of a sample (cell lysate or culture supernatant) was mixed with 50 mM citrate buffer (pH 4.8) containing cellobiose (15 mM), and the mixture was incubated at 60° C. for 2 hours. Then, the concentration of released reducing sugar was measured using the DNS (3,5-dinitrosalicylic acid) method, and one enzyme activity unit was defined as activity per mg protein.

Figure 9:
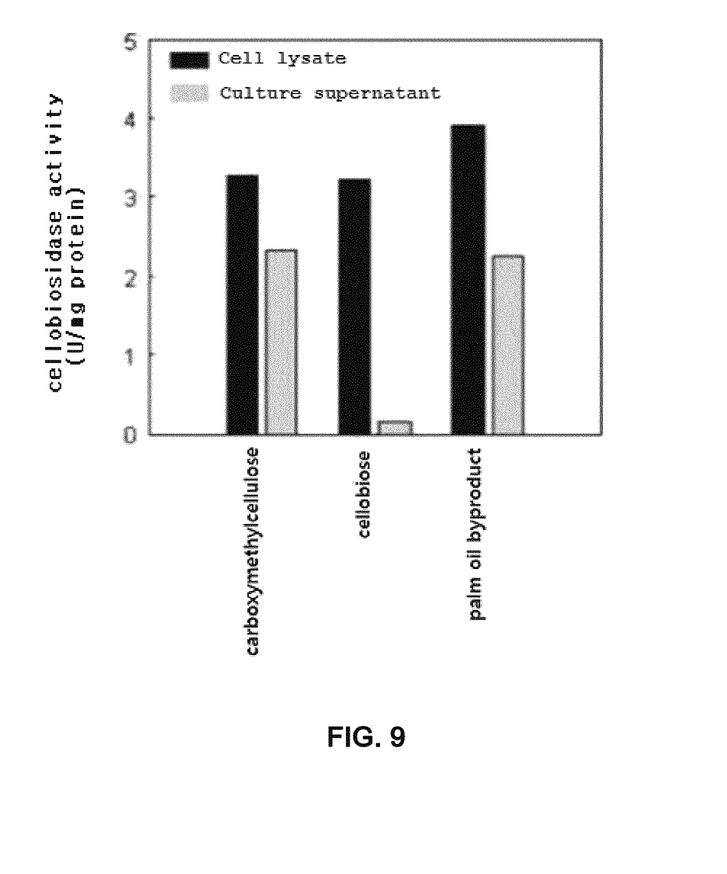
FIG. 9 is a graph showing the cellobiosidase activity of a culture of novel thraustochytrid-like microalgae KRS101 cultured using cellulosic biomass as a nutrient source.

As a result, as can be seen in FIG. 9, the activity of cellobiosidase was detected in the culture broth of the microalgal strain KRS101, even though it varied depending on the kind of cellulosic nutrient source. In addition, the use of the palm oil byproduct as the substrate showed the highest enzymatic activity.

[Deposit of Microorganisms]
Depository Institution: Korea Research Institute of Bioscience and Biotechnology;
Accession Number: KCTC11686BP;
Deposit Date: Apr. 22, 2010.

Industrial Applicability

As described above, the microalgae according to the present invention accumulate bio-oil at a high ratio in the cells when they are cultured in a glucose-containing medium, and thus can produce bio-oil in a high yield. In addition, the microalgae can produce bio-oil using bean powder as a nitrogen source, and a product obtained by culturing edible bean powder as a medium can be used as a raw material for producing food and feed. Also, the microalgae according to the present invention can produce bio-oil using non-food cellulosic biomass as a carbon source. Moreover, the use of non-food cellulosic biomass for the production of bio-oil can overcome the factors limiting the development of bio-oil, including the unstable supply of food resources and an increase in the cost of raw materials, and can improve the commercial competitiveness of microbial fermentation oil.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed:

1. A thraustochytrid-like microalgae KRS101 (KCTC11686BP) having the ability to produce bio-oil.

2. The thraustochytrid-like microalgae KRS101 (KCTC11686BP) of claim 1, which has 18S DNA nucleotide sequence of SEQ ID NO: 1.

3. The thraustochytrid-like microalgae KRS101 (KCTC11686BP) of claim 1, wherein the bio-oil comprises an unsaturated fatty acid.

4. The thraustochytrid-like microalgae KRS101 (KCTC11686BP) of claim 3, wherein the unsaturated fatty acid is docosahexaenoic acid (DHA).

5. The thraustochytrid-like microalgae KRS101 (KCTC11686BP) of claim 4, wherein the ratio of the content of docosahexaenoic acid (DHA) to the total content of fatty acids contained in the microalgae KRS101 is 40% or more.

6. A method for producing bio-oil, the method comprising the steps of:
 (a) culturing the thraustochytrid-like microalgae KRS101 (KCTC11686BP) of claim 1 to produce bio-oil; and
 (b) recovering the produced bio-oil.

7. The method of claim 6, wherein the bio-oil comprises an unsaturated fatty acid.

8. The method of claim 6, wherein the unsaturated fatty acid is docosahexaenoic acid (DHA).

9. A method for producing bio-oil, the method comprising the steps of:
 (a) culturing thraustochytrid-like microalgae KRS101 (KCTC11686BP) in a bean powder-containing medium to produce bio-oil; and
 (b) recovering the produced bio-oil.

10. The method of claim 9, wherein the medium contains bean powder as a single nitrogen source.

11. The method of claim 9, wherein the bio-oil comprises an unsaturated fatty acid.

12. The method of claim 11, wherein the unsaturated fatty acid is docosahexaenoic acid (DHA).

13. A method for producing bio-oil, the method comprising the steps of:
 (a) culturing thraustochytrid-like microalgae KRS101 (KCTC11686BP) in a cellulosic biomass-containing medium to produce bio-oil; and
 (b) recovering the produced bio-oil.

14. The method of claim 13, wherein the medium contains cellulosic biomass as a single carbon or nutrient source.

15. The method of claim 13, wherein the cellulosic biomass is selected from the group consisting of carboxymethylcellulose, cellobiose, and palm oil byproducts.

16. The method of claim 13, wherein the bio-oil comprises an unsaturated fatty acid.

17. The method of claim 16, wherein the unsaturated fatty acid is docosahexaenoic acid (DHA).

* * * * *

UNITED STATES PATENT AND TRADEMARK OFFICE
CERTIFICATE OF CORRECTION

PATENT NO.        : 8,617,857 B2                                    Page 1 of 1
APPLICATION NO.   : 13/695416
DATED             : December 31, 2013
INVENTOR(S)       : Jeong-Woo Seo It is certified that error appears in the above-identified patent and that said Letters Patent is hereby corrected as shown below:

On the Title Page, Item (54) and in the Specification, Column 1, line 1, the title
  "THRAUSTOCHYTRID-BASED MICROALGAE..."
should be
  --NOVEL THRAUSTOCHYTRID-BASED MICROALGAE...--

Signed and Sealed this
Fifteenth Day of April, 2014

Michelle K. Lee
*Deputy Director of the United States Patent and Trademark Office*